(12) United States Patent
Thiede et al.

(10) Patent No.: US 9,505,016 B2
(45) Date of Patent: Nov. 29, 2016

(54) MANUALLY OPERATED DISPENSER FOR MEDIA

(71) Applicant: MeadWestvaco Calmar GmbH, Hemer (DE)

(72) Inventors: Stephan Thiede, Lüdenscheid (DE); Thomas Gratzfeld, Iserlohn (DE); Gisbert Welp, Sundern (DE)

(73) Assignee: WestRock Dispensing Systems Hemer GmbH, Norcross, GA (US)

( * ) Notice: Subject to any disclaimer, the term of this patent is extended or adjusted under 35 U.S.C. 154(b) by 17 days.

(21) Appl. No.: 14/647,434

(22) PCT Filed: Nov. 25, 2013

(86) PCT No.: PCT/EP2013/003555
§ 371 (c)(1),
(2) Date: May 26, 2015

(87) PCT Pub. No.: WO2014/082727
PCT Pub. Date: Jun. 5, 2014

(65) Prior Publication Data
US 2015/0298151 A1 Oct. 22, 2015

(30) Foreign Application Priority Data

Nov. 28, 2012 (DE) ........................ 10 2012 023 215

(51) Int. Cl.
*B65D 88/54* (2006.01)
*B05B 11/00* (2006.01)
(Continued)

(52) U.S. Cl.
CPC ......... *B05B 11/3052* (2013.01); *A61M 11/007* (2014.02); *B05B 11/0005* (2013.01); *B05B 11/0037* (2013.01); *B05B 15/02* (2013.01); *B65D 83/40* (2013.01)

(58) Field of Classification Search
CPC ........... B05B 11/3052; B05B 11/0005; B05B 11/0037; B05B 5/02; A61M 11/0007

USPC ................................ 222/321.6–321.9, 402.1, 222/402.11–402.13; 604/249–302; 128/200.14, 200.23; 239/333, 322
See application file for complete search history.

(56) References Cited

U.S. PATENT DOCUMENTS

| 2,249,832 A | 7/1941 | Hubschman |
| 2,737,416 A | 3/1956 | Behr |

(Continued)

FOREIGN PATENT DOCUMENTS

| DE | 4400945 A1 | 7/1995 |
| DE | 10050981 A1 | 10/2000 |

(Continued)

OTHER PUBLICATIONS

International Search Report corresponding to PCT/EP2013/003555 dated Mar. 24, 2014, two pages.

(Continued)

*Primary Examiner* — Lien Ngo
(74) *Attorney, Agent, or Firm* — WestRock Intellectual Property Group

(57) ABSTRACT

Manually operated dispenser for media, with a reservoir (1), with a pump part (2) which is mounted on the reservoir (1) and comprises a nozzle-shaped discharge portion (3) with a discharge portion end (5) having a discharge opening (4), with an actuation mechanism (6) assigned to the pump part (2), and with a protective cap (7) covering at least the discharge portion end (5), wherein a soft porous insert (8) is inserted into the protective cap (7) and can be pressed when the protective cap (7) is fitted from above onto the discharge portion end (5), and the discharge portion (3) forms a stand surface (9) for a free end (10) of a torsion spring (11), which is clamped in the protective cap (7) and whose loading introduces a torque that turns the protective cap (7) relative to the discharge portion (3).

12 Claims, 4 Drawing Sheets

Figures 7, 8:
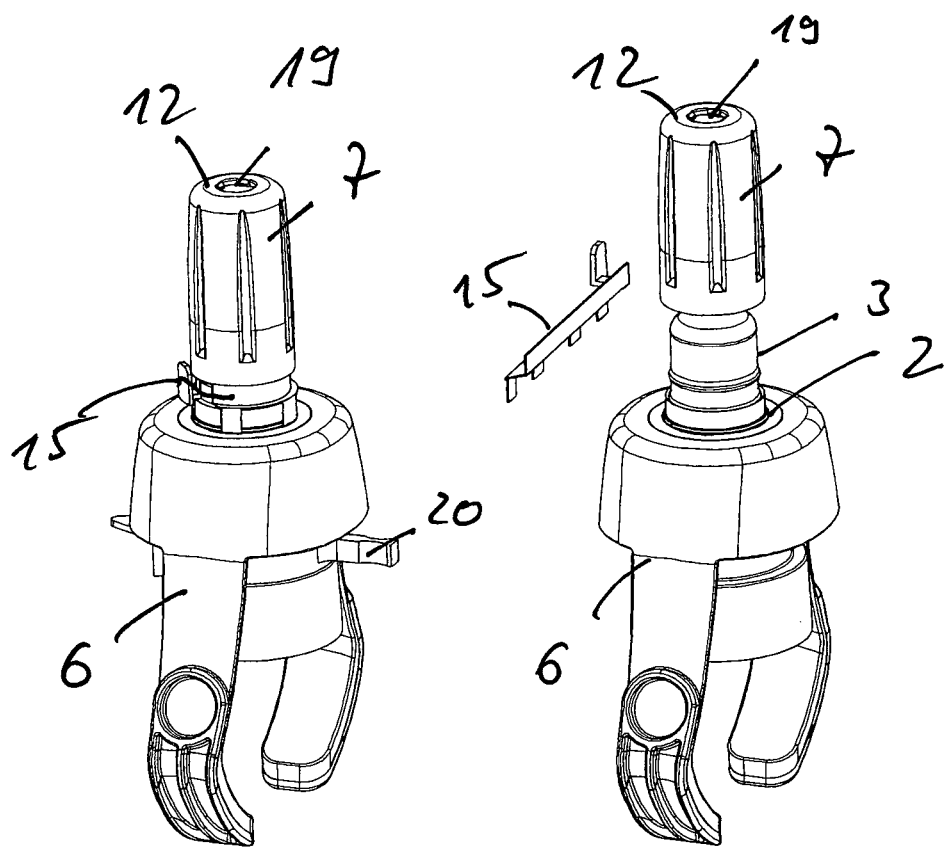

(51) Int. Cl.
  *B05B 15/02* (2006.01)
  *A61M 11/00* (2006.01)
  *B65D 83/40* (2006.01)

(56) References Cited

U.S. PATENT DOCUMENTS

| | | | | |
|---|---|---|---|---|
| 3,361,304 | A * | 1/1968 | Thompson | A61M 11/00 222/190 |
| 5,516,006 | A * | 5/1996 | Meshberg | A61M 15/08 222/162 |
| 5,971,226 | A * | 10/1999 | Goncalves | B65D 47/248 222/321.6 |
| 6,053,368 | A * | 4/2000 | Geimer | A61L 2/16 141/285 |
| 6,926,174 | B1 * | 8/2005 | Heldt | B05B 11/0027 215/321 |
| 7,044,341 | B2 * | 5/2006 | Sanchez | B05B 11/0027 222/321.6 |
| 8,062,264 | B2 * | 11/2011 | Godfrey | A61M 15/009 128/200.14 |
| 8,382,010 | B2 * | 2/2013 | Nadler | B05B 11/0016 222/321.1 |
| 2007/0262090 | A1 * | 11/2007 | Ritsche | B05B 11/0016 222/189.09 |
| 2012/0197219 | A1 * | 8/2012 | Scanlon | A61F 9/0008 604/295 |

FOREIGN PATENT DOCUMENTS

| | | |
|---|---|---|
| EP | 1020135 A1 | 7/2000 |
| FR | 2750406 A1 | 1/1998 |
| WO | WO 93/24164 A1 | 12/1993 |

OTHER PUBLICATIONS

English translation of International Preliminary Report on Patentability corresponding to PCT/EP2013/003555 dated Jun. 2, 2014.

* cited by examiner

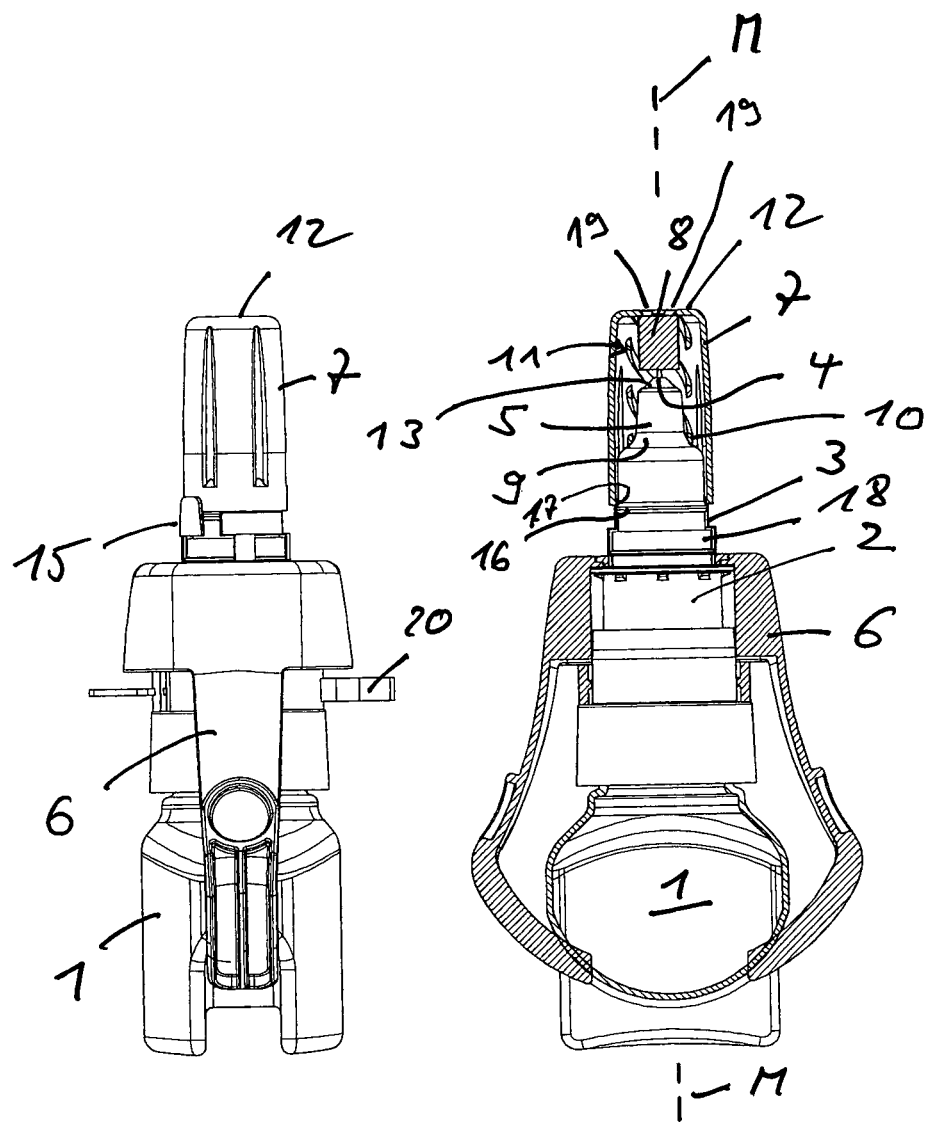

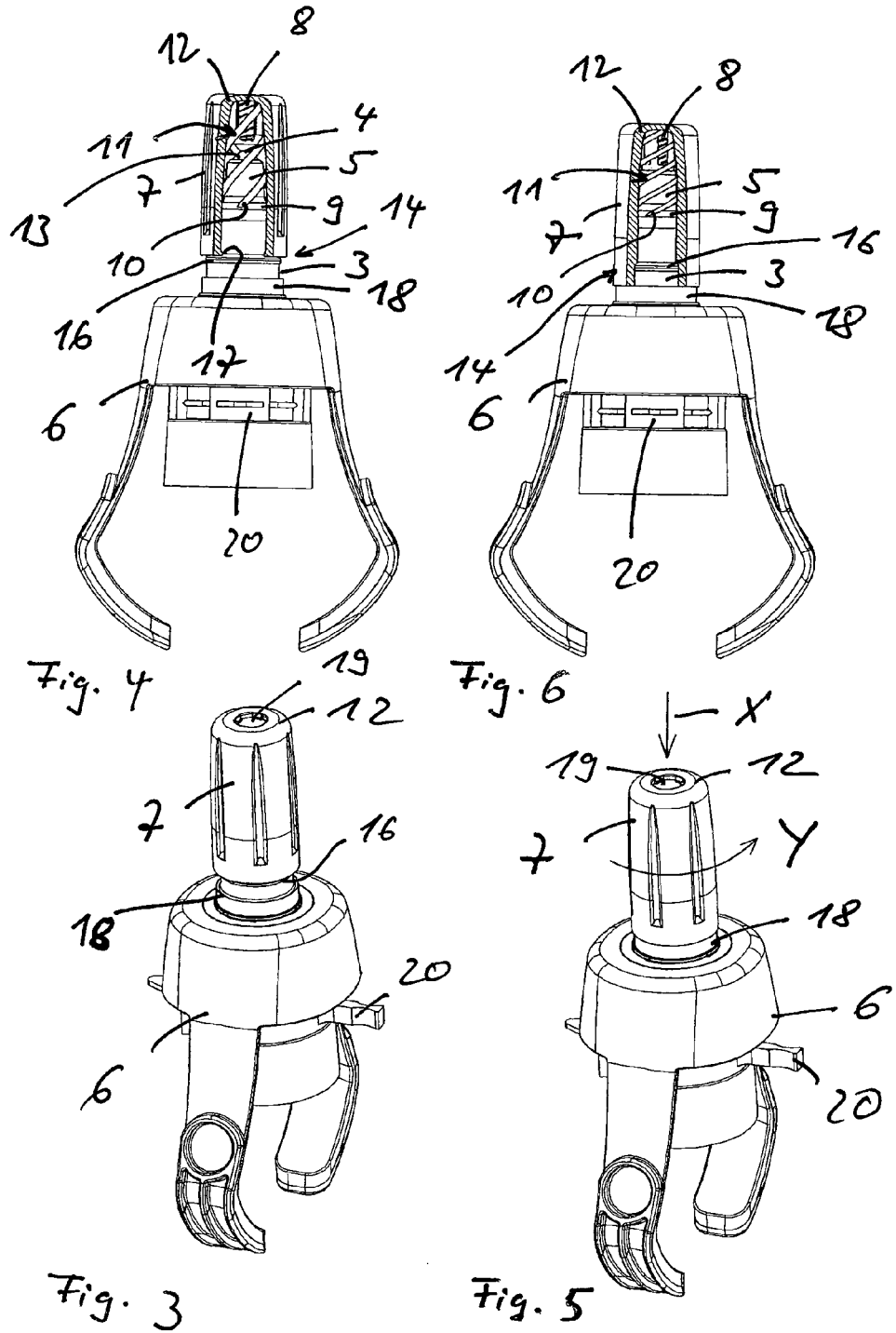

MANUALLY OPERATED DISPENSER FOR MEDIA

The invention relates to a manually operated dispenser for media in accordance with the preamble of claim 1.

DE 44 00 945 A1 discloses a dispensing device of this kind for fluid media. A fluid pump container is composed of a cylindrical fluid container on which a pump part, having a dosing pump, is sealingly mounted by means of a sealing ring. The dosing pump is operated by an actuation element, which is held in its upper rest position by an elastic force. Between the upper rest position and the lower actuation position, the actuation element is movable along an actuation path. For actuation, the actuation element has a plate-shaped portion. The dosing pump conveys the fluid from the fluid container through a vertical fluid channel, which continues axially upwards through the actuation element as far as an outlet opening arranged at the tip of the actuation element. The tip of the actuation element can be closed by a closure cap. A disadvantage is that the closure cap can, as a result of use, become soiled on the inside by fluid residues.

DE 100 50 982 A1 discloses a dispenser, in particular an atomizer for flowable substances, in particular pharmaceuticals, which dispenser uses a pump that has to be operated one or more times for priming. Its discharge nozzle is covered by a protective cap, which is suitable for collecting and storing the medium that is released during the priming strokes and before the start of the actual useful strokes. The protective cap is secured on the dispenser during the priming strokes. The protective cap is able to take up the amount of media that is sprayed, injected or dropped into it, e.g. in a sponge-like element. The protective cap is then removed for the actual actuation stroke. A storage space is formed in the protective cap since the latter, especially in its upper area, is at a greater distance from the nose adapter. In this storage space, a foam-like or sponge-like element is provided as storage means, which element is arranged in a ring shape surrounding the nose adapter. The storage space, which takes up the medium released during priming strokes, can be vented to the outside. The protective cap is used here as an intermediate storage for liquid medium in order to improve the dosing accuracy. The actual purpose of use of the protective cap, that of covering and protecting the discharge opening, is lost here, since the protective cap becomes a spray shield.

Known from WO 1993/024164 A1 is a device for administering liquid having a protective cap. The cap is provided with a soft, absorbent plug.

Known from DE 41 37 799 A1 is a dispenser for media having a protective cap. The protective cap of the dispenser is provided with a mounted torsion spring. Therefore, a valve body is elastically movable against the protective cap allowing a good sealing with the valve seating.

An object of the invention is therefore to make available a manually operated dispenser for media, in which the protective function of the protective cap for the discharge opening is improved.

This object is achieved by the features of claim 1.

A manually operated dispenser for media is thereby made available in which a protective cap, when fitted onto the dispenser, wipes the discharge portion end having the discharge opening. A soft porous insert absorbs media residues that have been left on the discharge portion end of the dispenser after use thereof. The torsion spring ensures a sufficient pressure force, which acts as a cleaning force. The torque introduced together with the pressure force follows the procedure typical for wiping movements, for example a rubbing movement. According to the invention, the soft and porous insert is used not only as a way of taking up medium, but also as a wiping device. The removal of residues of media can be used for cleaning purposes and also for analysis purposes.

By way of the torsion spring, in combination with a snap-fit connection provided for securing the protective cap on the discharge portion end, a forced movement for wiping the discharge portion end can be triggered when the protective cap is placed onto the dispenser. This forced movement can be triggered via a resilient length of the torsion movement that goes beyond the transition of the locking elements of the snap-fit connection. The manual pressure force needed for the snapping-in of the snap-fit connection then leads to an overshoot of the transition at which the protective cap with its insert is pressed against the discharge portion end and, as a result of the introduced torque, rubs across the discharge portion end.

Media residues, in particular liquid media residues, from previous dispensing procedures can thus be removed from the discharge opening when the protective cap is fitted. Drying off of the insert can be improved if the protective cap has vents, preferably in that area of the protective cap surrounding the insert.

The functional items sponge, membrane, nonwoven or other textile materials from natural or synthetic fibres are suitable, for example, as soft porous insert.

Further embodiments of the invention are set forth in the following description and in the dependent claims.

The invention is explained in more detail below on the basis of the illustrative embodiments shown in the attached figures.

Figure 9:
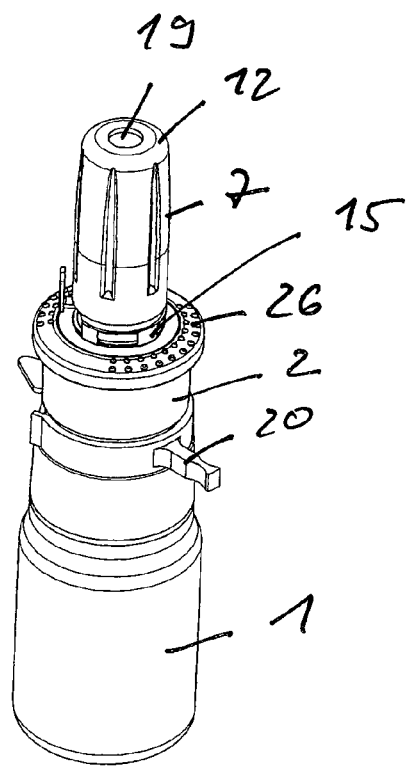
Figure 10:
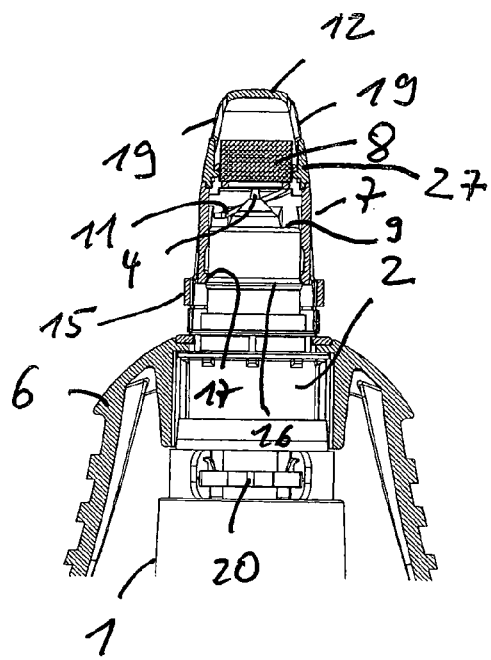
Figure 11:
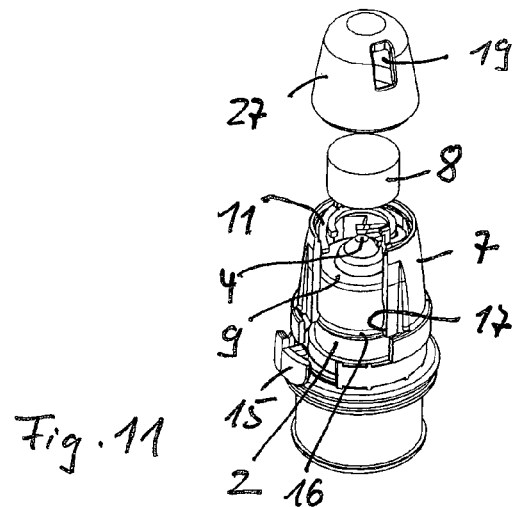

FIG. 1 shows a schematic side view of a manually operated dispenser according to a first illustrative embodiment, FIG. 2 shows a schematic cross section of FIG. 1, FIG. 3 shows a schematic perspective view of a partial area of the dispenser, with a protective cap fitted and after removal of a tear-off ring, FIG. 4 shows a schematic cross section of FIG. 3, FIG. 5 shows a schematic perspective view of a partial area of the dispenser with the protective cap pressed on, FIG. 6 shows a schematic cross section of FIG. 5, FIG. 7 and FIG. 8 show schematic perspective views of a partial area of the dispenser before and after the removal of a tear-off strip for a first use of the dispenser, FIG. 9 shows a schematic perspective view of a manually operated dispenser according to a second illustrative embodiment, FIG. 10 and FIG. 11 show a schematic cross section and a perspective and partially exploded view of a manually operated dispenser according to a third illustrative embodiment.

The invention relates to a manually operated dispenser for media, which dispenser is provided in particular for discharging a liquid medium, an aerosol or other fluid medium, if appropriate with solid fractions. The media are, for example, pharmaceuticals.

As FIG. 1 and FIG. 2 show, the dispenser comprises a reservoir 1 and pump part 2 mounted on the reservoir 1. The pump part 2 is movable relative to the reservoir 1 in a stroke direction, preferably between an upper rest position and a lower actuation position. The stroke direction has an axial orientation here.

The pump part 2 can be configured in a known manner, for example as described in DE 10 2008 027 598 A1.

As FIG. 2 shows, the pump part 2 comprises a nozzle-shaped discharge portion 3, with a discharge portion end 5 having a discharge opening 4. The pump part 2 is assigned an actuation mechanism 6, in order to discharge the medium by manual actuation of the actuation mechanism 6. For this purpose, the medium is stored in the reservoir 1, from which the medium is discharged by means of the pump part 2 through a media channel in the discharge portion 3 via individual pump strokes. The nozzle-shaped discharge portion 3 can have a different design, if appropriate also an ergonomic design, depending on the intended use, for example as nasal adapter or drop adapter. The pump part 2 and the reservoir 1 are here arranged coaxially.

For at least the discharge portion end 5, a covering protective cap 7 is provided, which is intended to protect the discharge opening 4, and the discharge portion end 5 surrounding the latter, when the dispenser is not in use. This is intended to avoid the dispenser being soiled and/or damaged in the area of the discharge of the medium.

The protective cap 7 is a preferably bushing-shaped lid which covers at least the discharge portion end 5 and which can repeatedly be firmly fitted in place after use of the dispenser.

As FIG. 2 to FIG. 5 show, a soft porous insert 8 is inserted into the protective cap 7 and can be pressed when the protective cap 7 is fitted from above onto the discharge portion end 5. The discharge portion 3 forms a stand surface 9 for a free end 10 of a torsion spring 11 clamped in the protective cap 7. The loading of the torsion spring 11, when the protective cap 7 is pressed onto the discharge portion end 5, introduces a torque that turns the protective cap 7 relative to the discharge portion 3. FIG. 5 illustrates the directions of the movement components by the arrows X and Y. The torsion spring 11 is loaded by the ends being pressed together. When loaded, the protective cap 7 turns about its longitudinal axis. The pivoting movement in the direction of the arrow Y about a rotation axis then preferably takes place about a centre axis M (cf. FIG. 2) of the pump part 2 and/or of the dispenser. The rotation angle is dependent on the length, preferably a number of windings or a torsion bar length, and diameter of the torsion spring and on the strength of the spring material used. Longer torsion springs 11 provide a greater rotation angle. A small rotation angle is generally sufficient, which can measure 0.5 to 3 mm, for example.

As FIG. 2 and FIG. 4 show, the interior of the protective cap 7 is equipped, adjacent to a protective cap wall 12 at the head end, with the soft porous insert 8, which is preferably designed like a cushion. The insert 8 then preferably has an axial extent into the interior of the protective cap 7, as a result of which the insert 8 yields and takes up fluid in the axial direction. The soft porous insert 8 can be designed as a sponge, membrane, nonwoven or other textile material from natural and/or synthetic fibres. For example, a PU foam, which has good absorbency, is particularly suitable as a sponge.

It is essential that the insert 8 takes up fluid when it is pressed against the discharge portion end 5 when the protective cap 7 is pressed on. If the insert 8 extends from the protective cap wall 12 at the head end into the interior of the protective cap 7 by an axial length, the insert 8 is pressed onto a head wall 13 of the discharge portion end 5 when the protective cap 7 is fitted in place and pressed on. The discharge opening 4 is arranged in the head wall 13. The insert 8 preferably has a radial extent that is greater than the diameter of the discharge opening 4, as is shown in FIG. 4. When pressed on, the insert 8 thus comes into contact with an area formed by the head wall 13 around the edge area of the discharge opening 4. Media residues left around the discharge opening 4 during a discharge stroke or spray procedure can thus be caught by the insert 8 and taken up. According to the invention, this pressing-on of the insert 8 in order to take up media residues from the discharge portion end 5 in the arrow direction X (cf. FIG. 5) is combined with a movement component in arrow direction Y, in order to generate as it were a rubbing and wiping movement, as a result of which the fluid uptake is improved.

The torsion spring 11 provided for this purpose is, for example, a torsion bar spring, helical spring or rubber spring. The torsion spring 11 is bar-shaped with a preferably axially directed resilient length in the interior of the protective cap 7. The insert 8 is preferably surrounded by the torsion spring 11. The insert 8 and the torsion spring 11 are then stressed jointly when the protective cap 7 is pressed on. The torsion spring 11 is therefore an elastic bar, of which one end is clamped on the protective cap 7, and a torque is introduced at the free end 10 thereof under a load. The effect of this is that the free end 10 turns at least about a small angle relative to the clamped end and therefore the loose protective cap 7, under an applied manual pressure force in arrow direction X, turns relative to the discharge portion 3 in arrow direction Y.

To accommodate the insert 8 and the torsion spring 11 in the interior of the protective cap 7, the protective cap 7 preferably has an excess length in relation to at least the discharge portion end 5 that is to be covered. When the protective cap 7 is fitted, preferably securely, in the state when the dispenser is not in use, the insert 8 and the torsion spring 11 are then unloaded or at least partially unloaded.

As is also shown in FIG. 3 to FIG. 6, the protective cap 7 can preferably be secured removably on the discharge portion 3 via a snap-fit connection 14. FIG. 4 shows the snap-fit elements of this snap-fit connection 14 before a first use and in an as yet unlocked state. Before the first use, a tear-off ring 15 is provided between the protective cap 7 and the actuation mechanism 6, in order to indicate a first use. FIG. 7 and FIG. 8 show the removal of the tear-off ring 15 for the first use. It is only after the tear-off ring 15 has been detached that the protective cap 7 can be removed and the pump part 2 can be operated in order to discharge medium.

As FIG. 4 shows, the snap-fit connection 14, as a segmented ring snap-fit connection on the discharge portion 3, comprises an outer bead 16 which is far from the end and is arranged as a shaped part. The protective cap 7 can lock releasably on the outer bead 16 like a lid via segmented inner ring snap-fit elements 17 near the end. Before the first use, shown in FIG. 4, there is no join between the outer bead 16 and the inner ring snap-fit elements 17, since the inner ring snap-fit elements 17 lie above the outer bead 16. Before a first use, there is no need for media residues to be wiped off.

As FIG. 6 shows by comparison with FIG. 5, the torsion spring 11 preferably has a resilient length that goes beyond the transition of the locking elements of the snap-fit connection 14 as defined by the outer bead 16 of the snap-fit connection 14. The resilient length of the torsion spring 11 is defined by a stop 18, which limits an overshoot path of the protective cap 7 relative to a snap-fit element, here the outer bead 16, on the discharge portion 3. When a manual force is applied to press the protective cap 7 into the snap-fit connection 14, an as it were forced overrun of the protective cap 7 as far as the stop 18 is generated. The torsion spring 11 also acts as a damping member, such that the generated rotation movement of the spring element leaves behind an elastic impression. The stop 18 can be formed separately from the discharge portion 3, since it need only be assigned to the latter. FIG. 5 shows the protective cap 7 in abutment against the stop 18. When the protective cap 7 is unloaded, it moves upwards until the inner ring snap-fit elements 17 engage behind the outer bead 16 as releasable join position (not shown). The torsion spring 11 holds the join position of the snap-fit connection 14 preferably under spring pretensioning.

The protective cap 7 can have one or more openings 19, in the area where the insert 8 is enclosed, in order to form an air-permeable closure. Here, the one or more openings 19 are arranged in the protective cap wall 12, for example. The protective cap 7 can thus be better ventilated for drying off the soft porous insert 8 during the time when the dispenser is not in use.

Examples of materials that can be used for the torsion spring 11 are polypropylene (PP), polyoxymethylene (POM) or polybutylene terephthalate (PBT). The covering length of the protective cap 7 relative to the discharge portion 3 can be chosen depending on the particular use. In the case of a nasal adapter, for example, a longer protective cap for coverage is provided than in the case of a drop adapter. In a known manner, an insertable actuation blocker 20 for the pump part 2 can be provided.

The soft porous insert 8 can also be a rod-shaped carrier, which can be exchangeable as a collector for filter purposes or analysis purposes, such as DNA determination.

FIG. 9 shows a second illustrative embodiment of a manually operated dispenser, which differs from the above-described illustrative embodiment in that another actuation mechanism 26 is provided for the pump part 2. The actuation mechanism 26 is designed here in a known manner as a handle plate. Otherwise, the above comments accordingly apply. The design of the protective cap 7 is independent of the nature and direction of the engaging actuation mechanism.

FIG. 10 and FIG. 11 show a third illustrative embodiment of a manually operated dispenser, which differs from the above-described first illustrative embodiment in that the protective cap 7 has a head portion 27 that can be applied releasably. This is advantageous especially if the insert 8 is frequently exchanged or is used as a collector for analysis purposes. It can then be the case that the insert 8 is exchanged after just one or a few pump strokes. The torsion spring 11 is then preferably short, for example 5 to 10 mm and/or only two to three windings, with the result that only a slight pivoting movement about the rotation axis occurs when the torsion spring 11 is loaded. This can be at least partially compensated by a voluminous insert 8 which, if elastic material is used on account of its compression behaviour, can combine an axial movement with pivoting movements. The absorbing and wiping effect thus obtained is good enough to take up media from the discharge opening 4 into the insert 8. For this purpose, the insert 8 can be a shaped insert which, for example, is shaped like a plug or a portion of a plug.

The invention claimed is:

1. A manually operated dispenser for media, with a reservoir, with a pump part which is mounted on the reservoir and comprises a nozzle-shaped discharge portion with a discharge portion end having a discharge opening, with an actuation mechanism (6, 26) assigned to the pump part, and with a protective cap covering at least the discharge portion end, wherein a soft porous insert is inserted into the protective cap and can be pressed when the protective cap is fitted from above onto the discharge portion end, and the discharge portion forms a stand surface for a free end of a torsion spring, which is clamped in the protective cap and whose loading introduces a torque that turns the protective cap relative to the discharge portion.

2. The manually operated dispenser according to claim 1, wherein the torsion spring is a torsion bar spring, helical spring or rubber spring.

3. The manually operated dispenser according to claim 1, wherein the soft porous insert is designed as sponge, membrane, nonwoven or other textile material from natural and/or synthetic fibres.

4. The manually operated dispenser according to claim 1, wherein the soft porous insert is designed like a cushion.

5. The manually operated dispenser according to claim 1, wherein the soft porous insert is surrounded by the torsion spring.

6. The manually operated dispenser according to claim 1, wherein that the protective cap can be secured removably on the discharge portion by a snap-fit connection.

7. The manually operated dispenser according to claim 6, wherein the snap-fit connection is designed as a segmented ring snap-fit connection.

8. The manually operated dispenser according to claim 6, wherein the torsion spring holds the joining position of the snap-fit connection under spring pretensioning.

9. The manually operated dispenser according to claim 6, wherein the torsion spring has a resilient length that goes beyond the transition of the locking elements of the snap-fit connection.

10. The manually operated dispenser according to claim 9, wherein the resilient length is limited by a stop, which limits an overshoot path of the protective cap relative to a snap-fit element on the discharge portion.

11. The manually operated dispenser according to claim 6, wherein an outer bead far from the end is arranged as shaped part on the discharge portion, on which outer bead the protective cap locks releasably like a lid via segmented inner ring snap-fit elements near the end.

12. The manually operated dispenser according to claim 1, wherein the protective cap has openings, in the area where the soft porous insert is enclosed, in order to form an air-permeable closure.

* * * * *